United States Patent
Williams

(10) Patent No.: US 8,332,042 B2
(45) Date of Patent: Dec. 11, 2012

(54) MEDICAL LEAD WITH STIFFENING COIL

(75) Inventor: Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 473 days.

(21) Appl. No.: 12/354,265

(22) Filed: Jan. 15, 2009

(65) Prior Publication Data
US 2010/0179630 A1  Jul. 15, 2010

(51) Int. Cl.
*A61N 1/00* (2006.01)
*A61B 5/04* (2006.01)

(52) U.S. Cl. ........ 607/115; 607/116; 607/122; 607/127; 600/373; 600/374; 600/375

(58) Field of Classification Search .......... 607/115–116, 607/122, 127; 600/373–375
See application file for complete search history.

(56) References Cited

U.S. PATENT DOCUMENTS

| | | | |
|---|---|---|---|
| 4,886,074 A | 12/1989 | Bisping | |
| 4,924,881 A * | 5/1990 | Brewer | 607/127 |
| 5,154,705 A | 10/1992 | Fleischhacker et al. | |
| 5,165,421 A | 11/1992 | Fleischhacker et al. | |
| 5,358,516 A * | 10/1994 | Myers et al. | 607/116 |
| 5,373,619 A | 12/1994 | Fleischhacker et al. | |
| 5,476,501 A | 12/1995 | Stewart et al. | |
| 5,678,296 A | 10/1997 | Fleischhacker et al. | |
| 5,984,877 A | 11/1999 | Fleischhacker, Jr. | |
| 6,210,395 B1 | 4/2001 | Fleischhacker et al. | |
| 6,516,230 B2 | 2/2003 | Williams et al. | |
| 6,685,696 B2 | 2/2004 | Fleischhacker et al. | |
| 6,920,361 B2 | 7/2005 | Williams | |
| 7,004,976 B2 * | 2/2006 | Ornberg et al. | 623/23.58 |
| 7,092,764 B2 | 8/2006 | Williams et al. | |
| 7,205,051 B2 * | 4/2007 | King et al. | 428/516 |
| 7,769,443 B2 * | 8/2010 | Barolat | 607/3 |
| 2003/0023294 A1 * | 1/2003 | Krall et al. | 607/122 |
| 2005/0069696 A1 * | 3/2005 | King et al. | 428/339 |
| 2008/0208248 A1 | 8/2008 | Rutten et al. | |
| 2008/0242964 A1 | 10/2008 | Horrigan et al. | |

FOREIGN PATENT DOCUMENTS

| | | |
|---|---|---|
| WO | WO-9421325 | 9/1994 |
| WO | WO 01/80941 A2 | 11/2001 |
| WO | WO 02/089909 A1 | 11/2002 |
| WO | WO 2006/135754 A1 | 12/2006 |
| WO | WO-2007079375 | 7/2007 |

OTHER PUBLICATIONS (PCT/US2010021116) PCT Notification of Transmittal of the International Search Report and the Written Opinion of the International Searching Authority.

* cited by examiner

*Primary Examiner* — Nicole F Lavert
(74) *Attorney, Agent, or Firm* — Reed A. Duthler; Stephen W. Bauer

(57) ABSTRACT

An implantable lead for a medical device includes a lead body having a proximal end and a distal end, an electrical connector coupled to the proximal end of the lead body, an electrode coupled to the distal end of the lead body, and electrically conductive conductor coil extending between the proximal and the distal end of the lead body, the conductor coil wound in a first winding direction under tension. The lead body also includes a plastic ribbon wound around the conductor coil in a second winding direction opposite to the first winding direction without releasing the tension of the conductor coil.

16 Claims, 3 Drawing Sheets

TABLE

| Turns | Torque for prior art lead | Torque for lead of present teachings |
|---|---|---|
| 0 | 0 | 0 |
| 1.0 | 0.008 | 0.030 |
| 1.5 | 0.015 | 0.043 |
| 2.0 | 0.018 | 0.055 |
| 2.5 | n/a | 0.069 |

MEDICAL LEAD WITH STIFFENING COIL

Implantable medical electrical leads can include one or more wires which are wound on a mandrel to form a conductor coil. The wires are wrapped with enough tension to cause the wires to exceed their yield point and thus to hold a coiled shape. The coil can be formed from multiple insulated wires as a multi-conductor coil. The lead body can be constructed with an outer polymeric sheath encasing the conductors, which may be arranged coaxially or co-linearly and insulated from one another. A distal end of each conductor can be coupled to one or more electrodes and a proximal end of each conductor can be coupled to a connector. The connector can be coupled to medical device for therapy delivery, such as, for example, an implantable pulse generator or an implantable cardioverter defibrillator or other medical device.

The distal end of the lead can be positioned at a target site within cardiac tissue so that the electrodes can electrical activity of the heart muscle and deliver pacing, defibrillation or other therapy. In active lead fixation, the electrode can include an anchoring portion or fixator, which is anchored at the target site by application of a torsional force transmitted to the fixator through the lead body.

SUMMARY

The present teachings provide an implantable lead for a medical device that includes a lead body having a proximal end and a distal end, an electrical connector coupled to the proximal end of the lead body, an electrode coupled to the distal end of the lead body, and electrically conductive conductor coil extending between the proximal and the distal end of the lead body, the conductor coil wound in a first winding direction under tension. The lead body also includes a plastic ribbon wound around the conductor coil in a second winding direction opposite to the first winding direction without releasing the tension of the conductor coil, the plastic ribbon forming a stiffening coil.

In another aspect, the present teachings provide an implantable lead for a medical device comprising a lead body having a longitudinal lumen, a proximal end and a distal end, a fiber core substantially made of Ultra High Molecular Weight Polyethylene (UHMWPE) within the longitudinal lumen of the lead body, and an electrically conductive conductor coil extending between the proximal and the distal end of the lead body, the conductor coil wound in a first winding direction over the fiber core. The lead also includes a plastic ribbon wound around the conductor coil in a second winding direction opposite to the first winding direction, the plastic ribbon keeping the conductor coil under stress and increasing the torsional stiffness of the lead body by about 300%.

The present teachings also provide a method of constructing a lead body for an implantable lead of a medical device comprising winding a conductor coil in a first winding direction under tension, winding a plastic ribbon over the conductor coil in a second winding direction opposite to the first winding direction without releasing the stress of the conductor coil, and covering the plastic ribbon and conductor coil with an insulation layer.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses.

The present teachings are applicable to any medical devices that are used with implantable and electrically conductive leads, including pacemakers, defibrillators or other medical devices providing rhythm management, resynchronization therapy, defibrillation or other cardiac therapy. The present teachings provide an electrically conductive lead that is constructed to have increased torsional stiffness relative to known leads of comparable diameter.

Figure 1:
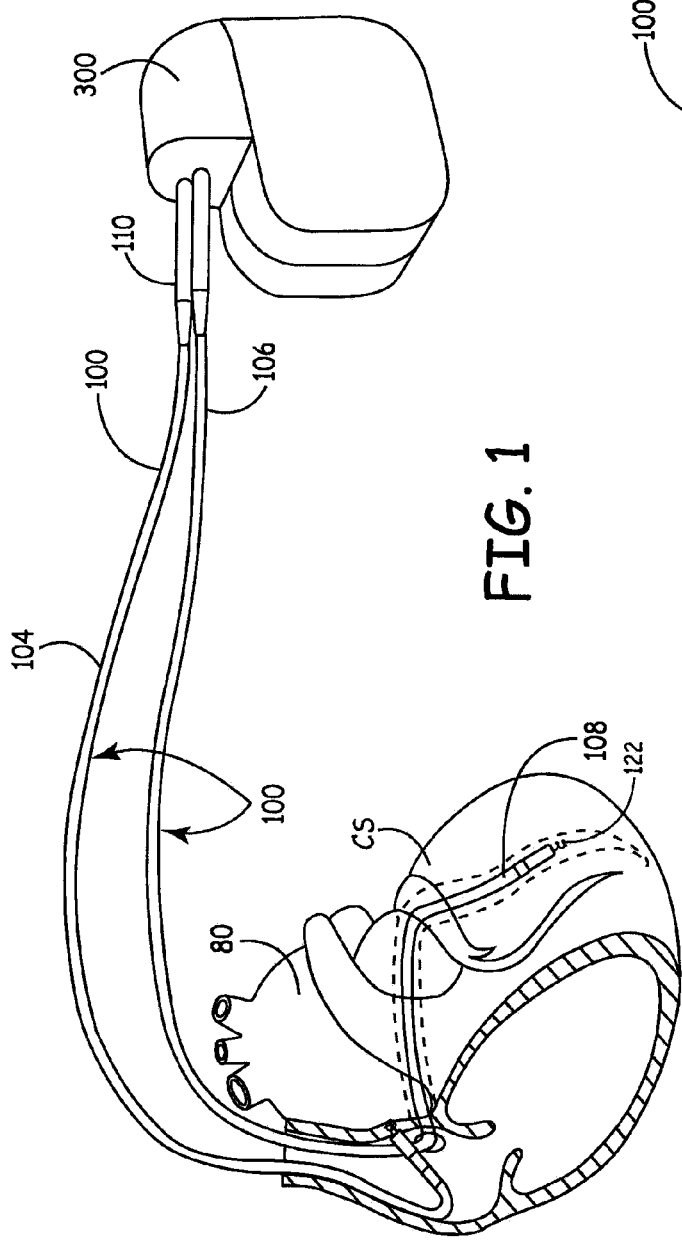
FIG. 1 is an environmental perspective view of a medical device including an implantable.

Referring to FIG. 1, an exemplary medical device 300 connected to and in electrical communication with an implantable electrically conductive lead 100 is shown in the context of an exemplary left heart application, although the present teachings are applicable to other cardiac procedures for reaching a targeted site for therapy delivery, including right or left heart procedures, epicardial, tranceptal, coronary sinus or other approaches to the target site. The lead 100 can be cannulated having an internal bore or lumen, a body 104, a proximal portion 106, and a distal portion 108. The proximal portion 106 can be coupled by a connector 110 to a connector block of the medical device 300. A catheter or other lead delivery device (not shown) can be used to facilitate insertion of the lead 100 through heart tissue 80 in a desired location or chamber of the heart.

Figure 2:
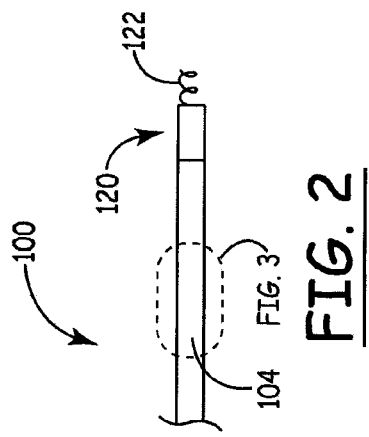
FIG. 2 is a side view of a distal portion of an exemplary implantable lead.
Figure 3:
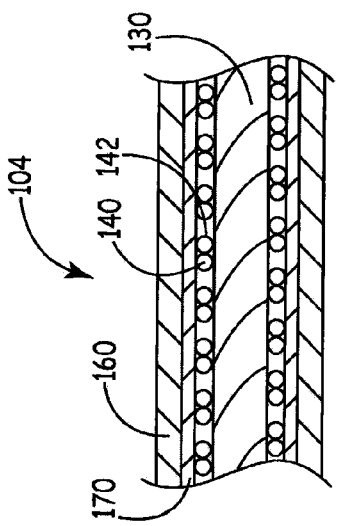
FIG. 3 is a sectional view of a detail of the implantable lead of FIG. 2 according to the present teachings.

Referring to FIGS. 2 and 3, a distal portion of an exemplary lead 100 for active fixation is illustrated. The lead 100 can include an electrode head 120 and an electrode 122 mounted on the electrode head 122. The electrode 122 can be in the form of an active fixator 122, such as a helix or screw, for active fixation into heart tissue at the desired stimulation or therapy site, as disclosed in U.S. Pat. No. 6,516,230 issued to Williams et al on Feb. 4, 2003, and incorporated herein by reference. It will be appreciated that other electrodes with different fixator configurations, active or passive, can also be used. Additionally, the active fixator 122 can be either non-retractable, or retractable, as disclosed in U.S. Pat. No. 5,476,501 issued to Stewart et al in Dec. 19, 1995, and incorporated herein by reference. The electrode 122 can be made of a biocompatible and highly conductive metal, such as, for example, platinum, or platinum-iridium alloy.

Figure 4:
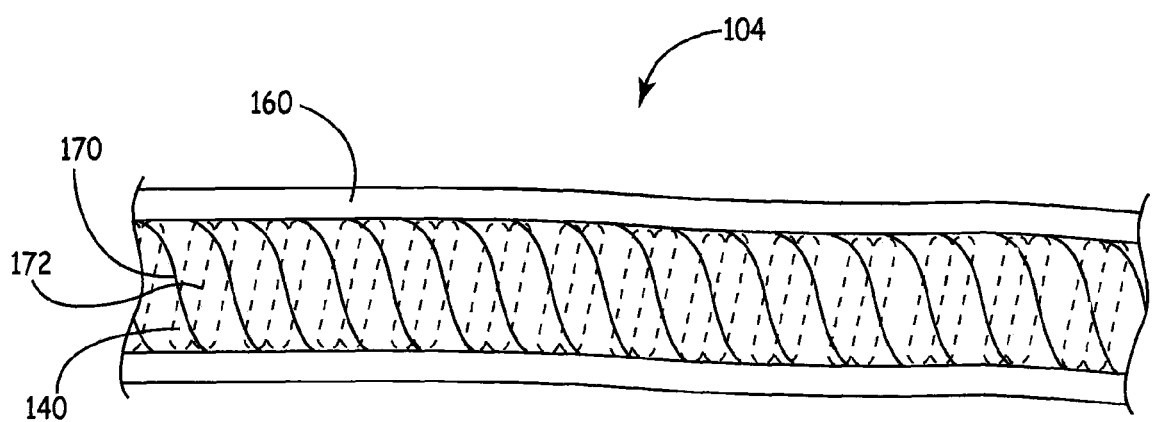
FIG. 4 is a side view of a detail of FIG. 2 according to the present teachings.

Referring to FIGS. 3 and 4, a sectional view of the body 104 of the lead 100 is illustrated. The lead 100 can optionally include a fiber core 130 surrounded by a conductor coil 140. When the fiber core 130 is not used, the conductor coil 140 can be wound around a removable mandrel. The conductor coil 140 can be monofilar, bifilar, as illustrated, or multifilar. The conductor coil 140 can be made of MP35N alloy (an alloy of Ni, Co, Cr, and Mo) with a silver core. The individual wires of the conductor coil 140 can have a diameter of about 0.003 inches. An outer insulation layer 160 can surround the conductor coil 140. The insulation layer 160 can be made of biocompatible polymer, such as silicone or polyurethane (e.g. 55D Pellethane polyurethane). The wire of the conductor coil 140 can include a coating 142 of a second biocompatible plastic material, such as polyimide, although PTFE or other material can also be used.

The conductor coil 140 can be wound around the fiber core 130, or, alternatively, around a removable mandrel, using a known winding machine, such as the coil winder produced by Accuwinder Engineering, San Dimas, Calif. The fiber core 130, when included, can be used as the mandrel around which the wire of the conductor coil 140 is wound, and retained as a tensile strength member in the finished lead 100. The conductor coil 140 can be wound around the fiber core 130/mandrel under tension. At the end of the winding process for the conductor coil 140, and according to the present teachings, the conductor coil 140 is not allowed to relax to its unrestricted diameter by cutting the coil, as is done in known conductor coils. Instead, the conductor coil 140 can be kept under tension while a layer of a high-modulus yarn or ribbon 170 is wound around the conductor coil 140 in the opposite winding direction, before releasing the tension of the conductor coil 140. The yarn 170 is wound in the opposite direction than the winding direction of the conductor coil 140, so that when the lead 140 is torqued for fixation of the electrode 122 at the target site, the torque is transferred to the tip of helical electrode 122 and does not act to expand the coiled yarn 170. Although the conductor coil 140 can tend to expand with the fixation torque, the expansion of the conductor coil 140 can be prevented by the yarn 170 that is wound around the conductor coil 140. Specifically, the fixation torque tends to contract the yarn 170, which can then compress the conductor coil 140.

The yarn 170 can be in the form of a substantially flat ribbon, having, for example, an aspect ratio of width to thickness of about 10:1. The yarn 170 can form a torque stiffening coil 172, which prevents the conductor coil 140 from expanding when the tension in the conductor coil 140 is released, thereby placing the conductor coil 140 in a torsionally prestressed state. The yarn 170 can be made of Ultra High Molecular Weight Polyethylene (UHMWPE), which has mechanical properties, such as modulus and percent elongation at yield, similar to those of steel wire. The stiffening coil 172, when made of UHMWPE yarn 170, can reduce the diameter of the conductor coil 140 from about 0.016 inches (0.40 mm) in the relaxed state, to about 0.015 inches (0.38 mm) in the stressed state, a reduction of about 5%. Similar reduction in diameter, while maintaining an equivalent torsional stiffness, cannot be obtained with metallic materials that match the strength of stainless steel, for example. A stiffening coil made of metal would have an increase in diameter of 0.008 inches (0.20 mm) and would be too large for delivery through a catheter of desirable diameter to the site, especially for a left heart implantation procedure. In contrast, the thickness of the yarn 170 is about 0.0015 inches (0.038 mm), resulting an a diameter increase of about 0.003 inches (0.076 mm)

The fiber core 130 can be formed of Ultra High Molecular Weight Polyethylene (UHMWPE) and can be, for example, in the form of a braid of four oval cross-section fibers, which can be compressed by the conductor coil 140 into a substantially circular cross-section fiber core 130. Alternatively, the fiber core 130 can be formed from a multi-fiber polyester core.

Figures 5, 6:
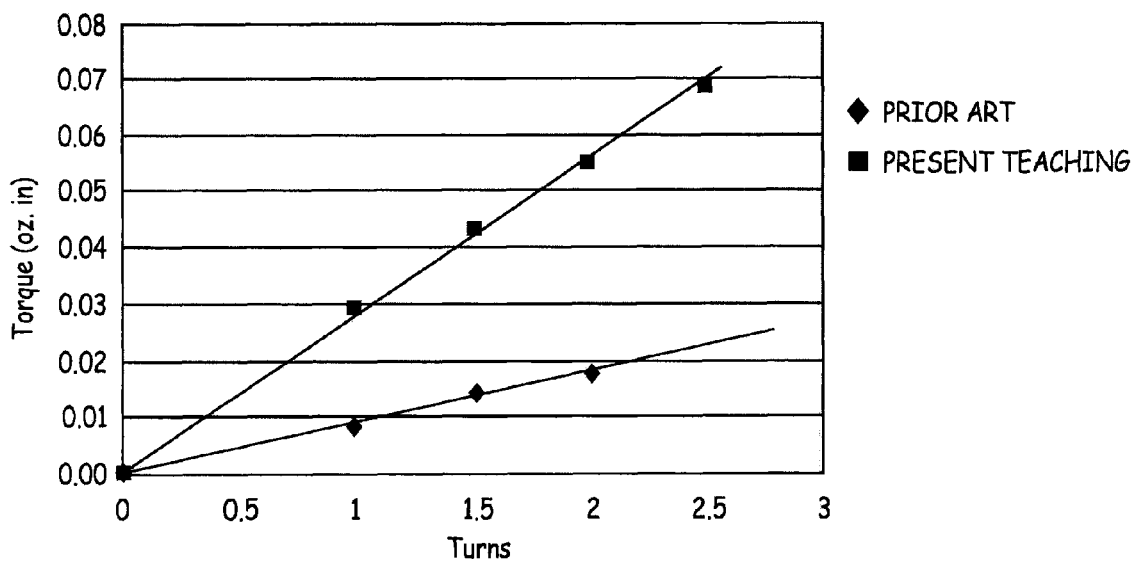
FIG. 5 is a Table of torques for prior art lead and lead according to the present teachings obtained experimentally.
FIG. 6 is a graphical representation of the data of the Table of FIG. 5.

A comparison of experimental results of the torsional stiffness of a sample of prior art lead, i.e., a lead without the stiffening coil 172 and a sample of lead 100 according to the present teaching, i.e., a lead with the stiffening coil 172, is illustrated in FIGS. 5 and 6. In the tests, a fiber core is included in both leads, the lead diameter of both leads is 2.6 French or 0.87 mm, and the sample lead body for the test is 12 inches. The stiffening coil 172 for the lead according to the present teachings is made of a yarn of Ultra High Molecular Weight Polyethylene (UHMWPE). As can be seen from the Table of FIG. 5 and the graph of FIG. 6, the torsional stiffness of the lead with the stiffening coil 172 can be approximately three times the torsional stiffness of the prior art lead that lack the stiffening coil 172 of the present teachings.

The increased torsional stiffness of the lead 100 according to the present teachings can facilitate helical fixation of the electrode 122 and can avoid the problem of the lead spiraling within a delivery catheter when torque is applied for fixation. Such spiraling can cause the lead to lock in the delivery catheter and prevent lead advancement and fixation. For this reason, prior art leads are used within a sleeve disposed between the lead and the delivery catheter, thereby requiring a bigger diameter catheter. The lead 100 according to the present teachings can be used without such a sleeve inside the delivery catheter. Accordingly, the delivery catheter can have a reduced diameter of 4 French or 1.33 mm and facilitate cardiac synchronization or other therapy via the coronary sinus or other approaches to the target site that require minimal outer diameter for the lead 100 and the delivery catheter. Smaller diameter leads can also be preferred for medical reasons, such as reducing venous occlusion, especially when multiple leads are required. Additionally, the lead 100 according to the present teachings can maintain fixation efficacy with a decreased diameter.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An implantable lead for a medical device comprising:
a lead body having a proximal end and a distal end;
an electrical connector coupled to the proximal end of the lead body;
an electrode coupled to the distal end of the lead body;
an electrically conductive conductor coil extending between the proximal and the distal end of the lead body, the conductor coil wound in a first winding direction under tension; and
a plastic ribbon wound around the conductor coil in a second winding direction opposite to the first winding direction without releasing the tension of the conductor coil, the plastic ribbon forming a stiffening coil.

2. An implantable lead for a medical device comprising:
a lead body having a proximal end and a distal end;
an electrical connector coupled to the proximal end of the lead body;
an electrode coupled to the distal end of the lead body;

an electrically conductive conductor coil extending between the proximal and the distal end of the lead body, the conductor coil wound in a first winding direction under tension; and a plastic ribbon wound around the conductor coil in a second winding direction opposite to the first winding direction without releasing the tension of the conductor coil, the plastic ribbon forming a stiffening coil; and the plastic ribbon made of Ultra High Molecular Weight Polyethylene (UHMWPE).

3. The implantable lead of claim 2, the plastic ribbon having a cross-sectional aspect ratio of about 10 to 1.

4. The implantable lead of claim 2, wherein the wire of the conductor coil includes a polyimide coating layer.

5. The implantable lead of claim 2, wherein the electrode comprises an active fixator.

6. The implantable lead of claim 5, wherein the active fixator includes a helical screw.

7. The implantable lead of claim 2, wherein the electrode comprises a retractable helical fixator.

8. An implantable lead for a medical device comprising:
a lead body having a proximal end and a distal end;
an electrical connector coupled to the proximal end of the lead body;
an electrode coupled to the distal end of the lead body;
an electrically conductive conductor coil extending between the proximal and the distal end of the lead body, the conductor coil wound in a first winding direction under tension; and
a plastic ribbon wound around the conductor coil in a second winding direction opposite to the first winding direction without releasing the tension of the conductor coil, the plastic ribbon forming a stiffening coil; and
the plastic ribbon made of Ultra High Molecular Weight Polyethylene (UHMWPE), the plastic ribbon reducing a diameter of the conductor coil by about 5% from a relaxed state to a stressed state.

9. An implantable lead for a medical device comprising:
a lead body having a proximal end and a distal end;
an electrical connector coupled to the proximal end of the lead body;
an electrode coupled to the distal end of the lead body;
an electrically conductive conductor coil extending between the proximal and the distal end of the lead body, the conductor coil wound in a first winding direction under tension; and
a plastic ribbon wound around the conductor coil in a second winding direction opposite to the first winding direction without releasing the tension of the conductor coil, the plastic ribbon forming a stiffening coil; and
the plastic ribbon made of Ultra High Molecular Weight Polyethylene (UHMWPE), the plastic ribbon reducing a diameter of the conductor coil from about 0.40 mm at a relaxed state to about 0.38 mm in a stressed state.

10. An implantable lead for a medical device comprising:
a lead body having a proximal end and a distal end;
an electrical connector coupled to the proximal end of the lead body;
an electrode coupled to the distal end of the lead body;
an electrically conductive conductor coil extending between the proximal and the distal end of the lead body, the conductor coil wound in a first winding direction under tension; and
a plastic ribbon wound around the conductor coil in a second winding direction opposite to the first winding direction without releasing the tension of the conductor coil, the plastic ribbon forming a stiffening coil;
the plastic ribbon made of Ultra High Molecular Weight Polyethylene (UHMWPE); and
further comprising a core extending between the proximal end and the distal end of the body, the conductor coil wound around the core.

11. The implantable lead of claim 10, wherein the core comprises Ultra High Molecular Weight Polyethylene (UHMWPE).

12. The implantable lead of claim 11, wherein the plastic ribbon increases the torsional stiffness of the lead body by about 300%.

13. An implantable lead for a medical device comprising:
a lead body having a longitudinal lumen, a proximal end and a distal end;
a fiber core comprising Ultra High Molecular Weight Polyethylene (UHMWPE) within the longitudinal lumen of the lead body;
an electrically conductive conductor coil extending between the proximal and the distal end of the lead body, the conductor coil wound in a first winding direction over the fiber core; and
a plastic ribbon wound around the conductor coil in a second winding direction opposite to the first winding direction, the plastic ribbon keeping the conductor coil under stress and increasing the torsional stiffness of the lead body by about 300%.

14. The implantable lead of claim 13, further comprising a layer of polyimide coating over the wire of the conductor coil.

15. The implantable lead of claim 13, further comprising an electrode with an active fixator coupled to the distal end of the lead body.

16. The implantable lead of claim 15, wherein the active fixator is a helical screw.

* * * * *